United States Patent [19]

Clarke et al.

[11] 4,179,567

[45] Dec. 18, 1979

[54] 2-ARYLTROPANE COMPOUNDS

[75] Inventors: Robert L. Clarke, Bethlehem; Sol J. Daum, Albany, both of N.Y.

[73] Assignee: Sterling Drug Inc., New York, N.Y.

[21] Appl. No.: 894,894

[22] Filed: Apr. 10, 1978

[51] Int. Cl.$^2$ .......................................... C07D 471/08
[52] U.S. Cl. ................................. 546/124; 546/125; 546/132; 546/63; 546/72; 424/265
[58] Field of Search ................ 260/292; 546/124, 125, 546/132

[56] References Cited

U.S. PATENT DOCUMENTS

3,073,831  1/1963  Archer et al. ........................ 260/292

OTHER PUBLICATIONS

Daum et al., Chem. Abstracts, vol. 83(9) Item No. 71,489r Sep. 1, 1975.

*Primary Examiner*—Alan L. Rotman
*Attorney, Agent, or Firm*—Thomas L. Johnson; B. Woodrow Wyatt

[57] ABSTRACT

Compounds of the tropane (8-azabicyclo[3.2.1]octane) series having an aromatic substiutent in the 2-position and a carboalkoxy group in the 3-position are prepared by reacting a tropane-3-carboxylate having a double bond in the 2,3-position with an aryl Grignard reagent. Transformations of the substituent on nitrogen are subsequently effected. Compounds where the 3-carboalkoxy group is in the exo configuration possess hypoglycemic activity, and those where the 3-carboalkoxy group is in the endo configuration possess narcotic antagonist activity.

42 Claims, No Drawings

2-ARYLTROPANE COMPOUNDS

BACKGROUND OF THE INVENTION (a) Field of the Invention

This invention relates to novel compounds of the tropane (8-azabicyclo[3.2.1]octane) series, in partricular tropanes having an aromatic substituent in the 2-position and a carboalkoxy group in the 3-position.

(b) Description of the Prior Art

Clarke and Daum U.S. Pat. No. 3,813,404, issued May 28, 1974 discloses tropane derivatives having the formula:

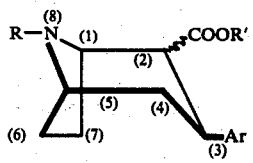

wherein Ar is phenyl or substituted phenyl, R is hydrogen or lower-alkyl, and R' is lower-alkyl. The compounds of the patent possess local anesthetic and central nervous system stimulant activities.

C. Kan-Fan et al., Acta Chemica Scand. 27, 1039 (1973), disclose an alkaloid isolated from a plant and having the structure:

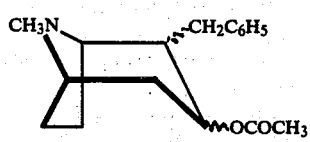

No physiological properties are disclosed for the latter compound in the reference.

SUMMARY OF THE INVENTION

In a composition of matter aspect, the invention relates to compounds of the formula:

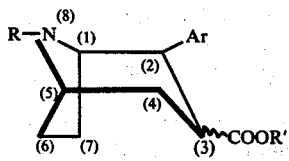

wherein:
R is selected from the group consisting of:
 hydrogen,
 alkyl of 1-8 carbon atoms optionally interrupted by an oxygen atom,
 phenylalkyl where alkyl has 1-3 carbon atoms,
 cyclopropylmethyl,
 hydroxyalkyl of 2-4 carbon atoms, and
 2,2-diethoxyethyl;
Ar is selected from the group consisting of:
 phenyl,
 benzyl,
 3-hydroxyphenyl,
 3-methoxyphenyl, and
 2-thienyl; and
R' is hydrogen or alkyl of 1 to 3 carbon atoms;
or pharmaceutically acceptable acid-addition salts thereof. Also included are several related compounds which fall outside the scope of the definitions of R and Ar given above.

In a further composition of matter aspect, the invention relates to compounds of the formula:

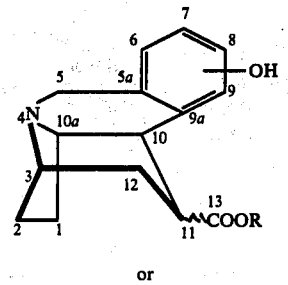

or

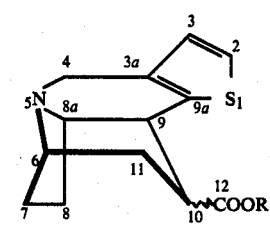

wherein R is alkyl of 1 to 3 carbon atoms, and the hydroxy group of II is in the 6- or 8-position of the pyrrolo[1,2-b]isoquinoline ring; or pharmaceutically acceptable acid-addition salts thereof. The compounds of Formulas II and III can be considered as variants of the compounds of Formula I wherein the group R represents a methylene bridge between the nitrogen atom and the aromatic nucleus.

In a process aspect, the invention relates to a process for preparing a compound of Formula I which comprises reacting a compound of the formula:

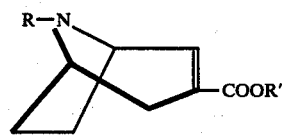

with ArMgX, where X is chlorine, bromine or iodine in an inert organic solvent under anhydrous conditions.

In a further process aspect, the invention relates to a process for preparing a compound of Formula I where R is other than hydrogen which comprises reacting a compound of Formula I where R is hydrogen with RX, where X is chlorine, bromine or iodine, in an inert organic solvent in the presence of a base.

DETAILED DESCRIPTION INCLUSIVE OF PREFERRED EMBODIMENTS

If derived by synthesis from natural sources, the compounds of the invention will be optically active. However, optically inactive racemic mixtures can be obtained by total synthesis and these in turn can be resolved by conventional procedures to obtain both optical isomers, one being identical to the enantiomer (1R) obtained from natural sources and the other the "unnatural" enantiomer (1S).

The compounds of Formulas I, II and III and related species are useful both in the free forms and in the form of acid-addition salts, and both forms are within the purview of the invention.

The acid-addition salts are simply a more convenient, water-soluble form for use, and in practice, use of the salt form inherently amounts to use of the base form. For pharmaceutical purposes, the acids which can be used to prepare the acid-addition salts include preferably those which produce, when combined with the free base, pharmaceutically acceptable salts, that is, salts whose anions are relatively innocuous to the animal organism in medicinal doses of the salts, so that the beneficial properties inherent in the free base are not vitiated by side-effects ascribable to the anions. Appropriate pharmaceutically acceptable salts within the scope of the invention are those derived from mineral acids such as hydrochloric acid, hydrobromic acid, hydriodic acid, nitric acid, phosphoric acid, sulfamic acid, and sulfuric acid; and organic acids such as acetic acid, citric acid, tartaric acid, lactic acid, cyclohexanesulfamic acid, methanesulfonic acid, ethanesulfonic acid, benzenesulfonic acid, p-toluenesulfonic acid, quinic acid, and the like, giving the hydrochloride, hydrobromide, hydriodide, nitrate, phosphate, sulfamate, acetate, citrate, tartrate, lactate, cyclohexanesulfamate, methanesulfonate, ethanesulfonate, benzenesulfonate, p-toluenesulfonate and quinate, respectively.

The acid-addition salts of said basic compounds are prepared either by dissolving the free base in aqueous or aqueous-alcohol solution containing the appropriate acid and isolating the salt by evaporating the solution, or by reacting the free base and acid in an organic solvent, in which case the salt separates directly or can be obtained by concentration of the solution.

The compounds can be prepared for use by dissolving under sterile conditions salt forms of the compounds in water (or an equivalent amount of a non-toxic acid if the free base is used), or in a physiologically compatible aqueous medium such as saline, and stored in ampoules for intramuscular injection. Alternatively, they can be incorporated in unit dosage form as tablets or capsules for oral administration either alone or in combination with suitable adjuvants such as calcium carbonate, starch, lactose, talc, magnesium stearate, gum acacia, and the like.

The molecular structures of the compounds of this invention were assigned on the basis of the methods of their synthesis and the study of their infrared and nuclear magnetic resonance (NMR) spectra, and confirmed by the correspondence between calculated and found values for the elementary analyses for representative examples.

The compounds of Formula I can be prepared by reacting a compound of the Formula IV with Ar-magnesium halide, where the halide is chloride, bromide or iodide, in an inert organic solvent under anhydrous conditions.

A preferred starting material is the known compound of Formula IV where R and R' are methyl.

The reaction of a compound of Formula IV with a Grignard reagent produces a mixture of two isomers of Formula I wherein the 3-carboalkoxy group is in the exo (beta or equatorial) configuration and the endo (alpha or axial) configuration which can be separated by fractional crystallization and/or column or plate chromatography.

Under basic conditions, as with sodium methoxide in methanol, equilibration of the epimers of Formula I occurs in which the exo epimer is preferentially formed. Thus the endo epimers can serve as intermediates for the exo epimers.

The compounds of Formula I or IV where R is hydrogen are prepared by differing methods, depending upon the nature of the Ar substituent. Because of steric hindrance, compounds of Formula I where R is methyl and Ar is phenyl or substituted phenyl are not readily demethylated by conventional means using such reagents as ethyl chloroformate or cyanogen bromide. Alternatively, these compounds are prepared by debenzylation of the compounds of Formula I where R is benzyl and Ar is phenyl or substituted phenyl. The debenzylation is carried out by catalytic hydrogenolysis. The debenzylation procedure cannot be used to prepare compounds of Formula I where R is hydrogen and Ar is 2-thienyl because the presence of sulfur poisons the catalyst. Fortunately, however, in this instance the ethyl diazoacetate N-demethylation procedure can be used, provided the diazoacetate adduct is hydrolyzed in a manner to avoid cyclization to form a compound of Formula III. A preferred hydrolysis reagent is hydrogen iodide in pyridine. In the event methanolic hydrochloric acid is used as the hydrolysis medium, the primary product is the cyclized compound III. Cyclized products of Formula II are prepared by an analogous procedure.

The compounds of Formula I where R is other than hydrogen or methyl can be prepared by alkylation of the compounds where R is hydrogen with R—X, where X is halogen, preferably bromine or iodine, in the presence of a base.

The compounds of Formula I can be further reacted with methylmagnesium halide to produce ketones wherein the 3-carboalkoxy group of Formula I is replaced by an acetyl group.

Pharmacological evaluation of the compounds of Formula I has shown that those wherein the 3-carboalkoxy group is in the exo (beta or equatorial) configuration possess hypoglycemic activity upon oral administration to experimental animals, the activity residing in the 1R optical enantiomer. The compounds are thus useful in counteracting high blood sugar levels such as are present in diabetic conditions.

The hypoglycemic activity in these compounds is accompanied by varying degrees of analgesic activity. This is an undesirable side-effect, but it can be counteracted by subcutaneous administration of a narcotic antagonist such as nalorphine prior to giving the hypoglycemic agent.

Hypoglycemic activity has also been found in compounds corresponding to Formula I wherein the equatorial 3-carboalkoxy group is replaced by an acetyl group; and in compounds of Formulas II and III when the carboalkoxy group is in the exo (equatorial) position.

The hypoglycemic activity was measured in fasted 100 g male Sprague-Dawley rats given either water or the test compound in water alone or with glucose (3 mg/kg orally) or with glucose plus glucagon (3 mg/kg subcutaneously). Blood samples were obtained from the tail vein at 0, 0.5, 1, 1.5 and 2 hours after treatment and were analyzed for glucose using a Technicon Auto Analyzer. By this procedure the compounds of Formula I of the exo configuration reduced the glucose blood levels by amounts varying from 20 to 80 percent, depending upon the specific compound used, at dose levels of 64–100 mg/kg ((calculated as free base, administered orally).

The analgesic activity was determined in rats by a modified D'Amour-Smith "tail flick" method described by Harris and Pierson, *J. Pharmacol. Exp. Ther.* 143, 141 (1964). Activities roughly equal to that of codeine were observed in the compounds of Formula I of the exo configuration. The analgesic activity was effectively blocked by administering 1 mg/kg of nalorphine subcutaneously 10 minutes prior to giving the test compound.

Pharmacological evaluation of the compounds of Formula I wherein the 3-carboalkoxy group is in the endo (alpha or axial) configuration has shown that they possess narcotic antagonist activity, devoid of demonstrable analgesic activity, and are thus useful in counteracting the effects of narcotics. The activity resides in the 1S optical enantiomer.

The narcotic antagonist activity was measured in rats by oral or subcutaneous administration according to the method of Harris and Pierson, loc. cit., using phenazocine, morphine or meperidine as the narcotic being antagonized. By this procedure the compounds of Formulas I and II of the endo configuration were shown to have narcotic antagonist activity vs pentazocine at $AD_{50}$ values ranging from 0.3 to 56 mg/kg upon subcutaneous as well as oral administration. The endo isomers are also effective as antagonists of the analgesic activity present in the exo isomers, without affecting the hypoglycemic activity in the latter. Thus, the mixture of exo and endo isomers, initially produced by the Grignard reaction, are useful as hypoglycemic agents without appreciable analgesic side-effects.

The following examples will further illustrate the invention without the latter being limited thereby.

EXAMPLE 1

Reaction of Methyl (1RS)-8-Methyl-8-azabicyclo[3.2.1]oct-2-ene-3-carboxylate with Phenylmagnesium Bromide (a) A solution of 48.5 g (0.268 mol) of compound IV (R and R' are methyl) in 200 ml of ether was added dropwise with stirring in 40 min. to 135 ml (0.40 mol) of 3 M phenylmagnesium bromide (in ether) in 350 ml of ether, the internal temperature being held at $-23°\pm2°$ C. The mixture was stirred at this temperature for 1 hr. and then poured into 500 ml of 2 N hydrochloric acid and 250 g of ice with vigorous stirring. The layers were separated and the water layer was washed with ether and made strongly alkaline with conc. ammonium hydroxide. Extraction with ether gave 68 g of oily product which was distilled. The products of interest (55.6 g) were collected at 116°–130° C. (0.25–0.35 mm). Gas chromatography (GC) showed a 52:48 ratio (3-exo:3-endo) of the major components. Dilution of this distillate with 50 ml of pentane and chilling gave 10.2 g of massive prisms. It was recrystallized twice by melting, dilution with 2 volumes of pentane, cooling and seeding to give methyl (1RS-exo,exo)-8-methyl-2-phenyl-8-azabicyclo[3.2.1]octane-3-carboxylate, m.p. 59°–61° C.; hydrochloride salt, m.p. 210°–211° C. (needles from acetone).

(b) A 6 g portion of the oily residue remaining after separation of the 10.2 g of prisms above was chromatographed on 27 preparative silica gel plates using multiple passes of a 1.5:20:78.5 i-PrNH₂-Et₂O-pentane solvent system. The less polar of the two major bands furnished 1.56 g of the 3-exo ester described in part (a) above. The more polar band yielded 2.93 g of oily methyl (1RS-2-exo-3-endo)-8-methyl-2-phenyl-8-azabicyclo[3.2.1]octane-3-carboxylate. Its hydrochloride salt had the m.p. 227° C. (decompn.), colorless plates from acetonitrile.

EXAMPLE 2

Epimerization of Methyl (1RS-2-exo-3-endo)-8-methyl-2-phenyl-8-azabicyclo[3.2.1]octane-3-carboxylate A solution of 10.0 g of the crude 52:48 mixture (by GC) of the exo and endo isomers produced directly from the Grignard reaction described above in Example 1 and 0.5 g of sodium methoxide in 50 ml of methanol was refluxed for 3 hr. and concentrated by warming in vacuo. Ether and brine were added, and the ether layer was washed with brine. Concentration of the ether layer gave an oil which, by GC analysis, consisted of 6% endo isomer (retention time 17.2 min.) and 94% exo isomer (retention time 18.8 min.). Treatment of the crude product with ethereal hydrogen chloride and dual recrystallization of the salt from acetone gave 5.1 g of pure exo ester hydrochloride, m.p. 210°–211.5° C.

EXAMPLE 3

Reaction of the 1R Enantiomer of Compound IV (R and R' are methyl) with PHenylmagnesium Bromide (a) A solution of 11.18 g (0.0619 mol) of the 1R (dextrorotatory) enantiomer of compound IV (R and R' are methyl) in ether was added to phenylmagnesium bromide in the manner described in Example 1(a). Distillation of the crude product gave 14.78 g (92%) of material which boiled at 115°–121° C. (0.2 mm), it being a mixture epimeric at C-3. This distillate was dissolved in 50 ml of boiling methanol and 18 ml of water was added. Cooling to 20° C. caused separation of needle clusters. Cooling at 0° C. and filtration (washed with 10 ml of the same solvent mixture) gave 4.39 g of methyl (1R-exo,exo)-8-methyl-2-phenyl-8-azabicyclo[3.2.1]octane-3-carboxylate, m.p. 90°–91° C., needles from aqueous methanol; $[\alpha]_D^{25} = -16.3°$ (2% in chloroform).

(b) The filtrate from collection of the levorotatory exo isomer of part (a) was concentrated in vacuo to remove methanol and the oily esters (11.0 g, 0.0424 mol) were extracted with ether. A solution of this oil in 20 ml of absolute ethanol was added to a solution of 15.96 g (0.0424 mol) of levorotatory (natural) dibenzoyltartaric acid monohydrate in 30 ml of absolute ethanol. After 4 hrs. at 25° C., the precipitate of needles was collected and air-dried. The resulting 7.24 g of salt of levorotatory exo isomer was treated with 10 ml of 2 N hydrochloric acid and the liberated dibenzoyltartaric acid was washed away with ether. Addition of conc. ammonium hydroxide to the aqueous solution followed by extraction with ether afforded 2.89 more of levorotatory exo isomer. The total of 7.28 g of the latter thus separated was dissolved in 24 ml of boiling methanol, 8 ml of warm water was added and the solution was cooled to give 6.07 g of pure levorotatory exo isomer. Dilution of the filtrate with 7 ml more water almost produced permanent cloudiness but very little further exo isomer separated.

The ethanolic filtrate from separation of the 7.24 g of dibenzoyltartrate salt of levorotatory exo isomer was concentrated by warming in vacuo (<60°), the residue was treated with 20 ml of 2 N hydrochloric acid and the liberated acid was removed with ether. Addition of conc. ammonium hydroxide to the aqueous layer and extraction with ether afforded 6.9 g of predominantly methyl (1R-2-exo-3-endo)-8-methyl-2-phenyl-8- azabicyclo[3.2.1]octane-3-carboxylate. GC analysis indicated 10% of the exo isomer was still present, but this was removed by fractional crystallization of the hydrochloride salt from methanol and further purification through the picrate salt, m.p. 202°–204° C. The free base was distilled to give the pure levorotatory endo isomer, b.p. 121°–123° C. (0.3 mm), $n_D^{24}=1.5379$; $[\alpha]_D^{25}=-38.7°$ (2% in chloroform).

EXAMPLE 4

Reaction of the 1S Enantiomer of Compound IV (R and R' are methyl) with Phenylmagnesium Bromide The procedure described in Example 3 above for the 1R enantiomer was applied to the 1S enantiomer. From 10.57 g (0.0584 mol) of 1S (levorotatory) compound IV (R and R' are methyl) were obtained 3.75 g of methyl (1S-exo,exo)-8-methyl-2-phenyl-8-azabicyclo[3.2.1]octane-3-carboxylate, m.p. 90°–91° C., needles from aqueous methanol, $[\alpha]_D^{25}=+16.6°$ (2% in chloroform); and 1.85 g of methyl (1S-2-exo-3-endo)-8-methyl-2-phenyl-8-azabicyclo[3.2.1]octane-3-carboxylate, b.p. 120°–123° C. (0.3 mm), $n_D^{24}=1.5378$, $[\alpha]_D^{25}=+38.9°$ (2% in chloroform); picrate, m.p. 201°–203° C., prisms and rods from methanol.

EXAMPLE 5

(a) Methyl (3-endo)-3-acetoxy-8-benzyl-8-azabicyclo[3.2.1]octane-3-carboxylate

Methyl (3-endo)-8-benzyl-3-hydroxy-8-azabicyclo[3.2.1]octane-3-carboxylate [Clarke et al., *J. Med. Chem.* 18, 102 (1975)] (42.0 g, 0.153 mol) was refluxed with 175 ml of acetic anhydride, the mixture was concentrated at up to 90° C. (10 mm) and the residual oil was diluted with 100 ml of ether. This solution was stirred with 100 ml of saturated aqueous sodium bicarbonate for 1 hr., 5 g of solid sodium bicarbonate was added, stirring was continued for 1 hr. and the ether layer was separated and dried. Concentration gave 46.9 g (97%) of methyl (3-endo)-3-acetoxy-8-benzyl-8-azabicyclo[3.2.1]octane-3-carboxylate as a colorless oil.

(b) Methyl 8-benzyl-8-azabicyclo[3.2.1]oct-2-ene-3-carboxylate (compound IV, R is benzyl, R' is methyl)

A vigorously swirled, non-homogeneous mixture of 46.8 g (0.148 mol) of the 3-acetoxy compound of part (a) and 50 ml of "Nujol" mineral oil at 100° C. was added in about 1 min. to 450 ml of stirred "Nujol" at 325° C. A stream of N₂ was blown onto the surface to remove liberated acetic acid. The internal temperature dropped to 310° C. but was back to 325° C. within 2 min. under external heating. After 4 minutes of reaction time, the mixture was poured into a large beaker to achieve rapid cooling. This mixture was diluted with 1 l. of ether and extracted with 200 and 100 ml of 2 N hydrochloric acid. The acid extracts were made alkaline with 35% sodium hydroxide and the liberated base was extracted with ether and distilled, b.p. 144°–149° C. (0.65 mm), 27.9 g (73%), $n_D^{25}=1.5542$.

(c) The compound of part (b) above (compound IV, R is benzyl, R' is methyl) was reacted with phenylmagnesium bromide according to the procedure of Example 1(a). GC on the crude, distilled product (b.p. 190°–209° C., 0.7 mm) showed a 1:1 mixture of 3-exo and 3-endo epimers. Partial separation was accomplished through formation of picrate salts. The picrate of the endo isomer crystallized from ethyl acetate solution upon addition of ether, and the mixture of bases from the filtrate was separated by silica gel chromatography. There was thus obtained a 33% yield of methyl (exo,exo)-8-benzyl-2-phenyl-8-azabicyclo[3.2.1]octane-3-carboxylate, m.p. 87°–88.5° C., prisms from methanol; and a 43% yield of methyl (2-exo-3-endo)-8-benzyl-2-phenyl-8-azabicyclo[3.2.1]octane-3-carboxylate as an oil.

EXAMPLE 6

(a) According to the procedure of Example 1, part (a), 18.1 g (0.10 mol) of compound IV (R and R' are methyl) was caused to react with a Grignard reagent prepared from 39.5 g (0.15 mol) of benzyl 3-bromophenyl ether, 4.9 g (0.20 g-atom) of magnesium and 200 ml of ether. The Grignard reagent and solvent formed 2 layers. The crude product was distilled rapidly (180°–215°/0.6 mm) giving 17.2 g of an oily epimeric mixture. Treatment of this oil in ether with excess ethereal hydrogen chloride and trituration of the precipitated salt with acetone gave 5.8 g of essentially pure axial epimer, methyl (2-exo-3-endo)-8-methyl-2-(3-benzyloxyphenyl)-8-azabicyclo[3.2.1]octane-3-carboxylate hydrochloride, m.p. 209° C. (decompn.), plates from acetonitrile.

The mother liquor from separation of the axial epimer was shown by NMR to contain 85% of the equatorial epimer. The oily base from this liquor crystallized. It was recrystallized from MeOH to give 6.78 g of methyl (exo,exo)-8-methyl-2-(3-benzyloxyphenyl)-8-azabicyclo[3.2.1]octane-3-carboxylate, m.p. 93°–94.5° C., needles from methanol.

(b) The epimeric benzyl ethers obtained in part (a) were hydrogenated in ethanol using 10% Pd/C under 60 psig hydrogen pressure. The 3-endo isomer was reduced in the form of its hydrochloride salt. One equivalent of 2 N hydrochloride was added to the reaction mixture containing the 3-exo isomer. Trituration with acetonitrile and with acetone caused crystallization of the following compounds, respectively: methyl (2-exo-3-endo)-8-methyl-2-(3-hydroxyphenyl)-8-azabicyclo[3.2.1]octane-3-carboxylate hydrochloride, m.p. 192°–193° C., prisms from acetonitrile; and methyl (exo,exo)-8-methyl-2-(3-hydroxyphenyl)-8-azabicyclo[3.2.1]octane-3-carboxylate hydrochloride, m.p. 238° C., prisms from ethanol.

EXAMPLE 7

According to the procedure of Example 1, part (a), 29.0 g (0.113 mol) of compound IV (R is benzyl, R' is methyl) and a Grignard reagent prepared from 63.5 g (0.24 mol) of benzyl 3-bromophenyl ether, 8.9 g (0.37 g-atom) of magnesium and 600 ml of ether. The Grignard reagent mixture formed 2 layers. After the quench process, addition of 2 N hydrochloric acid caused precipitation of product hydrochloride of low water solubility. The base was recovered by treatment with ammonium hydroxide and ether extraction. The crude, oily product 49.9 g (100%) was chromatographed on 2 kg of activity grade II–III Woelm basic alumina with rechromatography of the transitional fractions. The equatorial epimer was eluted ahead of the axial epimer to give, respectively, methyl (exo,exo)-8-benzyl-2-(3-benzyloxyphenyl)-8-azabicyclo[3.2.1]octane-3-carboxylate, and methyl (2-exo-3-endo)-8-benzyl-2-(3-benzyloxyphenyl)-8-azabicyclo[3.2.1]octane-3-carboxylate, both obtained as oils and used as intermediates in Example 19, below.

EXAMPLE 8

According to the procedure of Example 1, part (a), 10 g (0.055 mol) of compound IV (R and R' are methyl) and a Grignard reagent prepared from 25.8 g (0.14 mol) of m-bromoanisole and 4.0 g (0.16 g-atom) of magnesium in 120 ml of ether. The Grignard reagent partially precipitated as an oily layer. Distillation of the crude reaction product gave 7.0 g (50%) of a mixture of exo and endo epimers, b.p. 143°–147° C. (0.35 mm). A small quantity of the mixture of epimers was spread on silica preparative chromatoplates which were developed with 1:49:50 i-PrNH$_2$,EtOAc,pentane. The less polar epimer (endo-epimer) from the plates formed a crystalline HCl salt. The remainder of the epimeric mixture was treated with ethereal hydrogen chloride and the precipitated gum was triturated with acetone while seeding with the crystalline salt isolated above. The endo-ester (2.9 g) was collected and purified by one recrystallization from acetone, giving methyl (2-exo-3-endo)-8-methyl-2-(3-methoxyphenyl)-8-azabicyclo[3.2.1]octane-3-carboxylate hydrochloride, blades, m.p. 227°–228° C. (decompn.). Concentration of the filtrate to a small volume and cooling gave 1.9 g of exo-ester. One recrystallization from acetone purified it, giving methyl (exo,exo)-8-methyl-2-(3-methoxyphenyl)-8-azabicyclo[3.2.1]octane-3-carboxylate hydrochloride, m.p. 203°–204° C. (decompn.).

EXAMPLE 9

According to the procedure of Example 1, part (a), benzylmagnesium bromide (0.14 mol) was caused to react with compound IV (R and R' are methyl) (0.07 mol). The crude basic product (99%) was converted to a pasty salt with ethereal hydrogen chloride. Trituration with 40 ml of acetone and washing with 3×15 ml of this solvent afforded 17.7 g of crisp solid. Recrystallization from acetonitrile gave 11.7 g of methyl (2-exo-3-endo)-8-methyl-2-benzyl-8-azabicyclo[3.2.1]octane-3-carboxylate hydrochloride, plates, m.p. 218° C.

The mother liquor residue (4.63 g) from recrystallization of the endo-ester was a mixture of epimers. It was converted to the exo epimer by refluxing it with 2.0 g of sodium methoxide in 40 ml of methanol for 2 hrs., removing the solvent, adding water and extracting the product with ether. The oily base (3.06 g) crystallized. It was melted, diluted with an equal volume of pentane and allowed to crystallize to give pure methyl (exo,exo)-8-methyl-2-benzyl-8-azabicyclo[3.2.1]octane-3-carboxylate hydrochloride, plates, m.p. 222° C.

EXAMPLE 10

Following the procedure of Example 1(a), a mixture of C-3 epimers was prepared from 18.1 g (0.10 mol) of unsaturated compound IV (R and R' are methyl) and a Grignard reagent made from 24.5 g (0.15 mol) of 2-bromothiophene and 4.8 g (0.2 g-atom) of magnesium using ether as solvent. Distillation of the crude basic product gave 20.47 g (77%) of a 1:1 epimer mixture, b.p. 111°–122° C. (0.2 mm). The hydrochloride salt, formed with ethereal hydrogen chloride was triturated with acetone and then recrystallized from 35 ml of acetonitrile with cooling only to 30° C. Needle tufts separated (5.1 g) which were recrystallized from acetonitrile to give methyl (1RS-exo,exo)-8-methyl-2-(2-thienyl)-8-azabicyclo[3.2.1]octane-3-carboxylate hydrochloride, plates, m.p. 197°–198° C.

Concentration of the mother liquor from separation of the exo epimer gave 5.9 g of a mixture of needles and plates. Recrystallization of this solid from acetone afforded 5.0 g of a 45:55 mixture of hydrochlorides of the exo- and endo-esters, respectively, m.p. 168°–169° C.

When a crude, distilled, epimermic mixture obtained as above (92.6 g) was dissolved in 400 ml of methanol, treated with 2.9 g of sodium methoxide and refluxed for 3.5 hrs. under N$_2$, removal of the solvent and extraction of the basic ester with ether gave 92 g of a sticky crystalline mixture which (by NMR) contained 95% of the exo (equatorial) ester and 5% of the endo (axial) epimer. It was placed in a funnel and 125 ml of 1:1 ether-pentane was percolated through it, thereby leaving 74.9 g of essentially pure exo-epimer. Concentration of the percolate to a 25 ml volume and cooling gave 8.34 g more exo-epimer (total of 83.3 g, 96%).

EXAMPLE 11

Resolution of Methyl (1RS-exo,exo)-8-methyl-2-(2-thienyl)-8-azabicyclo[3.2.1]octane-3-carboxylate To a solution of 58.5 g (0.20 mol) of (−)-diacetone-2-ketogulonic acid monohydrate in 2.8 l. of ether was added 26.3 g (0.099 mol) of the racemic 3-exo epimer obtained in Example 10. The solution was boiled down to a 400 ml volume and the precipitate was collected at room temperature and washed with 25 ml of ether; 40.0 g, m.p. 141°–143.5° C. This solid was recrystallized from 2.5 l. of ether boiled down to a 125 ml volume to give 35.3 g of a salt containing one molecule of (−)-base and two molecules of the (−)-gulonic acid, m.p. 144°–145.5° C. and a second crop of 1.8 g of the same melting point; 37.1 g, 92%. Another recrystallization gave the (−)-diacetone-2-keto-L-gulonic acid salt of methyl (1R-exo,exo)-8-methyl-2-(2-thienyl)-8-azabicyclo[3.2.1]octane-3-carboxylate, m.p. 145°–146° C., $[\alpha]_D^{25} = -36.5°$ (1% in ethanol).

The (−)-base was liberated from this gulonate salt with 2 N sodium hydroxide and extracted with ether. Addition of ethereal hydrogen chloride to this extract, trituration of the precipitated hydrochloride salt with acetone and recrystallization from acetonitrile gave 9.4 g (3 crops) of hydrochloride salt. A second recrystallization from acetonitrile gave 8.3 g of the levo-rotatory hydrochloride salt of methyl (1R-exo,exo)-8-methyl-2-(2-thienyl)-8-azabicyclo[3.2.1]octane-3-carboxylate, prisms, m.p. 212°–214° C., $[\alpha]_D^{25} = -70.7°$ (1% in water).

The total mother liquors from purification of the initially precipitated 40.0 g of (−)-base salt above were treated with base to collect the remaining impure (−)-base (2.5 g). A solution of this base in 10 ml of warm absolute ethanol was added to a solution of 3.54 g of (−)-dibenzoyltartaric acid monohydride in 40 ml of absolute ethanol and the precipitated salt was collected at 25° C.; 5.6 g, m.p. 175° C. (dec.). This salt was treated with 7 ml of 2 N hydrochloric acid, the liberated acid was extracted with ether and the aqueous layer was made basic with conc. ammonium hydroxide. The liberated (−)-base (2.3 g) was recrystallized from cyclohexane to give 2.06 g of massive prisms of methyl (1R-exo,exo)-8-methyl-2-(2-thienyl)-8-azabicyclo[3.2.1]octane-3-carboxylate, m.p. 106°–107° C., $[\alpha]_D^{25} = -70.1°$ (1% in chloroform).

The ethereal filtrate from separation of the 40 g of (−)-base salt was treated with 70 ml of 2 N sodium hydroxide and the layers were separated. The aqueous layer was extracted once with ether and the ether layers were concentrated to give 12.7 g of impure, crystalline (+)-base. It was dissolved in 50 ml of warm absolute ethanol and added to a warm solution of 18.0 g of (+)-dibenzoyltartaric acid in 200 ml of absolute ethanol. The precipitated salt was collected at room temperature and washed with 2 portions of ethanol to give 28.1 g of the dibenzoyltartrate salt of methyl (1S-exo,exo)-8-methyl-2-(2-thienyl)-8-azabicyclo[3.2.1]octane-3-carboxylate, m.p. 174° C. (from ethanol), $[\alpha]_D^{25} = +106.8°$ (1% in pyridine).

The 28.1 g of salt was treated with 40 ml of 2 N hydrochloric acid and the liberated acid was washed away with ether. Basification of the aqueous layer with conc. ammonium hydroxide and ether extraction gave 11.66 g of dextro base, m.p. 97°–104° C. Recrystallization from cyclohexane afforded 10.7 g of methyl (1S-exo,exo)-8-methyl-2-(2-thienyl)-8-azabicyclo[3.2.1]octane-3-carboxylate, prisms, m.p. 104°–106.5° C., $[\alpha]_D^{25} = +69.8°$ (1% in chloroform); hydrochloride salt, m.p. 213°–214° C., prisms from acetonitrile, $[\alpha]_D^{25} = +70.6°$ (1% in water).

EXAMPLE 12

Methyl (exo,exo)-8-benzyl-2-(2-thienyl)-8-azabicyclo[3.2.1]octane-3-carboxylate was prepared from methyl 8-benzyl-8-azabicyclo[3.2.1]oct-2-ene-3-carboxylate (38.5 g, 0.150 mol) (Example 5b) and 2-thienylmagnesium bromide (0.22 mol) according to the procedure of Example 1, part (a). Distillation of the basic material isolated gave a forerun of 20.4 g collected at 136°–182° C. (0.5 mm), most of which was starting material (50% recovery). The desired product was collected rapidly at 182°–196° C. (0.5 mm) as a mixture, epimeric at C-3 (13.1 g, 26%).

Conversion of the mixture to the 3-exo epimer was done by refluxing the 13.1 g of mixture in 50 ml of MeOH containing 0.5 g of sodium methoxide for 2 hrs. Massive prisms precipitated during the process. The solvent was removed in vacuo and the residue was treated with 75 ml of methylene dichloride, 75 ml of ether and 5 ml of water in that order and shaken. The organic layer was washed with brine, dried over sodium sulfate and concentrated to give 12.6 g of crystalline solid. Two crystallizations gave 9.65 g of methyl (exo,exo)-8-benzyl-2-(2-thienyl)-8-azabicyclo[3.2.1]octane-3-carboxylate, prisms from methanol, m.p. 138°–140° C.

EXAMPLE 13

According to the procedure of Example 1, part (a), 2-pyrrolylmagnesium bromide [prepared from 33.5 g (0.50 mol) of pyrrole and 168 ml (0.50 mol) of ethereal 3 M methylmagnesium bromide in 200 ml of ether] was caused to react with 30.0 g (0.167 mol) of compound IV (R and R' are methyl) in 190 ml of ether. Distillation of the crude product gave 19.4 g (47%) of oil, b.p. 108°–131° C. (0.3–0.4 mm), $n_D^{25} = 1.5342$.

The oily product in 750 ml of ether was treated with excess ethereal hydrogen chloride and the precipitated salt was triturated with two 100 ml portions of acetone. Filtration gave 15.2 g of crystalline salt which was recrystallized from 1.5 l. of acetonitrile with concentration to a 750 ml volume. Prisms (9.78 g) separated which were recrystallized a second time from 200 ml of absolute ether with concentration to a 40 ml volume to give 8.10 g of methyl (2-exo-3-endo)-8-methyl-2-(1H-2-pyrrolyl)-8-azabicyclo[3.2.1]octane-3-carboxylate hydrochloride, m.p. 232°–234° C.

The filtrate from recrystallization of the 15.2 g of salt above was concentrated and the basic material was liberated with concentrated ammonium hydroxide. The resulting 3.94 g of oil in 25 ml of methanol was heated under reflux with 0.25 g of sodium methoxide ($N_2$ atmosphere) for 1.5 hrs. Concentration of the mixture by warming in vacuo, addition of 1 ml of water and extraction with ether gave 3.53 g of oil which, upon dilution with pentane, precipitated 1.27 g of methyl (exo,exo)-8-methyl-2-(1H-2-pyrrolyl)-8-azabicyclo[3.2.1]octane-3-carboxylate. Chromatography of the filtrate residue on 8 preparative silica gel plates using two solvent passes of 2:2:46:50 i-$PrNH_2$, MeOH, $CHCl_3$ and pentane gave 0.56 g more of this same epimer as the less polar of two significant bands. Recrystallization of the total 1.83 g twice from ethanol gave 1.34 g of pure 3-exo isomer, m.p. 113°–114° C.

EXAMPLE 14

(exo,exo)-8-Methyl-2-phenyl-8-azabicyclo[3.2.1]octane-3-carboxylic acid, hydrochloride salt methanolate, m.p. 240°–244° C., prisms from methanol, was prepared by hydrolysis of the corresponding methyl ester of Example 1(a) using refluxing 2 N hydrochloric acid (21 hrs.).

Similarly, the 3-endo methyl ester of Example 1(b) was hydrolyzed to give (2-exo-3-endo)-8-methyl-2-phenyl-8-azabicyclo[3.2.1]octane-3-carboxylic acid, hydrochloride salt, m.p. 258°–259° C. (vac.), prisms from methanol.

EXAMPLE 15

A solution of 12.5 g (0.044 mol) of a 1:1 mixture of the 3-exo and 3-endo acids obtained in Example 14 in 150 ml of isopropyl alcohol was treated with gaseous hydrogen chloride at reflux for 5 hrs. Concentration of the solution, treatment with excess 2 N sodium hydroxide and extraction with ether gave a mixture of esters (13.3 g, 92%) which was converted to the hydrochloride salts with ethereal hydrogen chloride. When the powdery salt mixture was dissolved in 50 ml of warm acetonitrile, plates precipitated spontaneously. Cooling below 25° C. caused coprecipitation of needles so filtration was done at 25° C. to give 4.6 g of pure plates of isopropyl (2-exo-3-endo)-8-methyl-2-phenyl-8-azabicyclo[3.2.1]octane-3-carboxylate, hydrochloride salt, m.p. 249° C. (vac.) (from acetonitrile). Dilution of the 20 ml mother liquor with 25 ml of ether precipitated 4.7 g (66%) of isopropyl (exo,exo)-8-methyl-2-phenyl-8-azabicyclo[3.2.1]octane-3-carboxylate, needles, hydrochloride salt, m.p. 217°–218° C. (decompn.).

EXAMPLE 16

Ethyl (exo,exo)-8-methyl-2-(2-thienyl)-8-azabicyclo[3.2.1]octane-3-carboxylate, b.p. 123°–126° C. (0.1 mm), $n_D^{25} = 1.5380$, was prepared by hydrolysis of the corresponding methyl ester of Example 10 according to the procedure of Example 14 and esterification of the resulting free acid with ethanol according to the procedure of Example 15.

EXAMPLE 17

1-Propyl (exo,exo)-8-methyl-2-(2-thienyl)-8-azabicyclo[3.2.1]octane-3-carboxylate A solution of 7.0 g (0.024 mol) of the acid produced from hydrolysis of the methyl ester of Example 10 (see Example 16) in 37 ml of 2 N sodium hydroxide was concentrated to a residue in vacuo. The resulting sodium salt was suspended in 65 ml of hexamethylphosphorus triamide (HMPA), 16.6 g (0.098 mol) of 1-propyl iodide was added and the mixture was stirred at room temperature for 40 hrs. Most of the HMPA was removed by distillation at a bath temperature of 150° C. using 1.5 mm pressure. The residue was stirred with 150 ml of ether, the mixture was filtered and the filtrate was washed with six 50 ml portions of water. Concentration of the filtrate and distillation of the residue gave 5.17 g of the n-propyl ester, b.p. 136°–150° C. (0.3 mm), $n_D^{25} = 1.5330$.

EXAMPLE 18

Methyl (exo,exo)-2-phenyl-8-azabicyclo[3.2.1]octane-3-carboxylate, hydrochloride salt, needles from acetonitrile, m.p. 244°–245° C. (decompn.); and methyl (2-exo-3-endo)-2-phenyl-8-azabicyclo[3.2.1]octane-3-carboxylate, sulfate salt hemihydrate, prisms from acetone, m.p. 93.5°–96.5° C. were prepared by hydrogenation of the corresponding 8-benzyl compounds of Example 5, part (c), in ethanol in the presence of one equivalent of 2 N aqueous hydrochloric acid using 1 g of 10% palladium-on-carbon catalyst per 6 g of amine with hydrogen under 60 psig.

EXAMPLE 19

Methyl (1RS-exo,exo)-2-(3-hydroxyphenyl)-8-azabicyclo[3.2.1]octane-3-carboxylate, hydrochloride salt, m.p. 234°–236° C. (decompn.), from methanol-ether; and methyl (1RS-2-exo-3-endo)-2-(3-hydroxyphenyl)-8-azabicyclo[3.2.1]octane-3-carboxylate, hydrochloride salt, m.p. 220°–222° C., from ethanol, were prepared by hydrogenation of corresponding N-benzyl-O-benzyl ethers obtained in Example 7, in ethanol containing 1 equivalent of 2 N hydrochloric acid using 10% palladium-on-carbon catalyst and 60 psig hydrogen.

Resolution of the 3-endo epimer: To a solution of 6.37 g (0.0218 mol) of (−)-diacetone-2-ketogulonic acid monohydrate in 23 ml of absolute ethanol at 40° C. was added 5.69 g (0.0218 mol) of the (1RS-2-exo-3-endo) compound obtained above. The latter dissolved and there was almost immediate precipitation of (+)-base.(−) gulonate salt. The solution was chilled and the precipitate collected and washed with three 1 ml portions of cold ethanol; 6.20 g. This salt was treated with 50 ml of water and 15 ml of conc. ammonium hydroxide and the crystalline product was collected; 2.71 g (95%). One recrystallization from ethanol gave 2.54 g of analytically and optically pure methyl (1S-2-exo-3-endo)-2-(3-hydroxyphenyl)-8-azabicyclo[3.2.1]octane-3-carboxylate, plates, m.p. 221°–222.5° C., $[\alpha]_D^{25} = +93.4°$ (1% in dimethylformamide); hydrochloride salt ⅓ ethanolate, prisms, m.p. 138.5°–139.5° C., $[\alpha]_D^{25} = +63.5°$ (1% in water).

The alcoholic filtrate and washings from separation of the (+)-base salt above were concentrated to a residue by warming in vacuo and the residue was treated with 25 ml of water and 15 ml of conc. ammonium hydroxide to give 2.79 g (98%) of crystalline product.

One recrystallization from EtOH gave 2.52 g of analytically and optically pure methyl (1R-2-exo-3-endo)-2-(3-hydroxyphenyl)-8-azabicyclo[3.2.1]octane-3-carboxylate, plates, m.p. 222°–223.5° C., $[\alpha]_D^{25} = -94.7°$ (1% in dimethylformamide); hydrochloride salt ⅓ ethanolate, prisms, m.p. 138.5°–139.5° C., $[\alpha]_D^{25} = -64.4°$ (1% in water).

EXAMPLE 20

(a) Diethyl 1-[(exo,exo)-3-Methoxycarbonyl-2-(2-thienyl)-8-azabicyclo[3.2.1]octan-8-ylmethyl]-1,2-hydrazinedicarboxylate A mixture of 16.5 g (0.062 mol) of methyl (1RS-exo,exo)-8-methyl-2-(2-thienyl)-8-azabicyclo[3.2.1]octane-3-carboxylate (Example 10), 50 g (0.29 mol) of diethyl azodicarboxylate and 150 ml of dry benzene was heated under reflux for 8 hr. Later experiments revealed that 2 moles of azo-ester per mole of tropane were adequate for this reaction. The product was extracted with 35, 25 and 25 ml of ice cold 2 N hydrochloric acid and each extract was washed quickly with ether and drained into a single flask containing 15 ml of concentrated ammonium hydroxide and 15 g of ice. Ether extraction of the liberated base gave 27.4 g of oily compound which was about 95% pure by TLC (silica, 3:97 i-PrNH$_2$-Et$_2$O). This product was used satisfactorily in the following reaction.

(b) A solution of 262.8 g (0.598 mol) of the adduct obtained in part (a) above in 1600 ml of methanol, 320 ml of pyridine and 500 ml of water was chilled to 15° C., divided into two portions, and each was treated with 220 ml of cold (5° C.) 47% aqueous hydrogen iodide. The resulting solutions were left at room temperature for three days and then concentrated to solid residues by warming to 60° C. in vacuo. Each residue was slurried with 175 ml of water, the slurries were filtered, and the filter cakes were washed with two 25 ml portions of water and air-dried.

Trituration of the combined crystalline solids (246 g) with a mixture of 100 ml each of concentrated ammonium hydroxide and water, agitation of the mixture with 600 ml of ether, and filtration separated 68.7 g of crystalline diethyl 1,2-hydrazinedicarboxylate. The layers of the filtrate were separated, the water layer was extracted with ether and the combined ether layers were concentrated to a residual oil in order to remove ammonia. Dilution of the oily residue with ether, addition of excess gaseous hydrogen chloride and collection of the precipitated crystalline salt gave 108.0 g (62%) of methyl (exo,exo)-2-(2-thienyl)-8-azabicyclo[3.2.1]octane-3-carboxylate hydrochloride, m.p. 235°–236° C. with intumescene. Recrystallization from acetonitrile (90 ml/g and concentrated to 25% of volume) afforded a sample with m.p. 239°–240° C. (intumescence).

EXAMPLE 21

(exo,exo)-2-(2-Thienyl)-8-azabicyclo[3.2.1]octane-3-carboxylic acid hydrochloride A solution of 3.0 g (0.01 mol) of the methyl ester obtained in Example 20(b) in 40 ml of 4 N hydrochloric acid was heated under reflux for 16 hrs. and concentrated to a residue by warming in vacuo. Trituration with acetonitrile produced a crystalline product which was recrystallized by dissolving it in 10 ml of boiling ethanol, filtering, cooling and adding 10 ml of ether.

Massive prisms separated (1.88 g) which melted at 209°–212° C. with intumescence after being dried for 2 hrs. at 55° C. (1 mm).

EXAMPLE 22

Ethyl (exo,exo)-2-(2-thienyl)-8-azabicyclo[3.2.1]octane-3-carboxylate was made from methyl ester obtained in Example 20(b) by hydrolysis and reesterification. A solution of 5.0 g (0.02 mol) of said methyl ester in 100 ml of 2 N hydrochloric acid was heated under reflux for 24 hrs. and then concentrated to a residual solid by warming in vacuo. This solid in 50 ml of absolute ethanol was saturated with hydrogen chloride gas and then heated under gentle reflux for 4 hrs. with a continuing stream of hydrogen chloride. Concentration of the solution by warming in vacuo and recrystallization of the residue from ethanol furnished 4.15 g of the hydrochloride salt of the title compound, m.p. 267°–268° C. (decompn.) with a second crop of 0.4 g which melted 1° lower.

EXAMPLE 23

A solution of 2.0 g (4.5 mmol) of the adduct obtained in Example 20, part (a) in 50 ml of methanol was saturated with gaseous hydrogen chloride without cooling and the solution was then heated under reflux with a slow stream of hydrogen chloride bubbled in for 2.5 hrs. After standing for 18 hrs. at room temperature the solution was concentrated by warming in vacuo and 25 ml of water was added. Filtration separated some crystalline diethyl hydrazodicarboxylate. Basification of the filtrate with concentrated ammonium hydroxide and extraction with ether separated 1.43 g of basic material which was chromatographed on five 20×40-cm silica preparative plates using two solvent passes of 2% i-PrNH$_2$-98% Et$_2$O. The band containing the major product, methyl (9a/12-Z)-4,6,7,8,8a,9-hexahydro-6,9-ethanothieno[3,2-f]indolizine-10-carboxylate (III; R is CH$_3$), afforded 0.95 g (79%) of colorless, crystalline solid, m.p. 97°–104° C. The hydrochloride salt formed needles from acetonitrile, m.p. 240°–241° C. (dec.); ethiodide (from free base and ethyl iodide), needles from ethanol, m.p. 247°–249° C. (decompn.); N-oxide (from free base and m-chloroperbenzoic acid), monohydrate from acetone, m.p. 162°–165° C.

EXAMPLE 24

Treatment of Methyl (exo,exo)-8-Methyl-2-[3-(benzyloxy)phenyl]-8-azabicyclo[3.2.1]octane-3-carboxylate with Diethyl Azodicarboxylate A mixture of 7.45 g (0.020 mol) of the exo-ester of Example 6, 7.10 g (0.040 mol) of diethyl azodicarboxylate and 30 ml of freshly boiled benzene was heated under reflux for 16 hrs. The cooled reaction solution was extracted with three 10 ml portions of 2 N hydrochloric acid and the combined extracts were treated with 10 ml of concentrated and 150 ml of 4 N hydrochloric acid. Reflux of the 4 N solution for 4 hrs. caused formation of benzyl chloride which was then removed by extraction with ether. Concentration of the aqueous solution by warming in vacuo gave a pasty solid which was swirled with 20 ml of methanol and again concentrated to remove residual water.

The solid carboxylic acid hydrochloride present at this point was dissolved in 200 ml of methanol and the solution was saturated with gasous hydrogen chloride and allowed to stand for 17 hrs. Filtration to remove a small amount of white powder and concentration of the filtrate by warming in vacuo gave an oil which crystallized in the presence of 25 ml of acetonitrile. The collected solid was treated with excess 2 N sodium hydroxide and ether, the clear layers were separated and the alkaline layer was immediately treated with excess gaseous carbon dioxide. Extraction with ether and concentration of the extracts to a small volume caused precipitation of 1.23 g (22%) of prisms of methyl (9a/13-Z)-1,2,10,10a-tetrahydro-8-hydroxy-3H,5H-3,10-ethanopyrrolo[1,2-b]isoquinoline-12-carboxylate (II; R is methyl, OH at 8), m.p. 206°–209° C. Recrystallization from 100 ml of acetone concentrated to a 15 ml volume furnished 1.05 g of needles, m.p. 210°–212° C.

EXAMPLE 25

Treatment of Methyl (2-exo-3-endo)-8-Methyl-2-[3-(benzyloxy)phenyl]-8-azabicyclo[3.2.1]octane-3-carboxylate with Diethyl Azodicarboxylate A mixture of 3.44 g (0.0094 mol) of the endo-ester of Example 6, 4.0 g (0.023 mol) of diethyl azodicarboxylate and 25 ml of freshly boiled benzene was refluxed and worked up as described in Example 24. The crude phenolic product precipitated from alkaline solution by carbon dioxide (1.78 g) was chromatographed on ten 20×40-cm silica preparative plates which were developed by three passes of 3:97 i-PrNH$_2$-Et$_2$O. The largest band (R$_f$ about 0.25) was eluted with acetone and the solution was concentrated to precipitate 0.77 g (30%) of colorless plates of methyl (9a/13-E)-1,2,10,10a-tetrahydro-8-hydroxy-3H,5H-3,10-ethanopyrrolo[1,2-b]isoquinoline-12-carboxylate (II; R is methyl, OH at 8), m.p. 213°–215° C. with slight darkening. Recrystallization from 100 ml of acetone boiled down to a 15 ml volume gave 0.67 g of m.p. 216°–218° C.

In the plate chromatography described above a band of R$_f$ about 0.07 was scraped and eluted. This material was rechromatographed to give 18 mg (7%) of crystalline methyl (9a/13-E)-1,2,10,10a-tetrahydro-6-hydroxy-3H,5H-3,10-ethanopyrrolo[1,2-b]isoquinoline-12-carboxylate (II; R is methyl, OH at 6), m.p. 217°–224° C.

EXAMPLE 26

To a mixture of 7.18 g (0.029 mol) of methyl (2-exo-3-endo)-2-phenyl-8-azabicyclo[3.2.1]octane-3-carboxylate sulfate (Example 18), 8.4 g (0.1 mol) of solid sodium bicarbonate and 50 ml of dimethylformamide was added 8.1 g (0.06 mol) of cyclopropylmethyl bromide. The mixture was stirred on the steam bath for 1 hr., stripped of solvent by warming in vacuo and extracted with ether. Hydrogen chloride was bubbled into the ether solution and the precipitated gummy salt was triturated with 2×25 ml of ethyl acetate and 3×10 ml of acetone to give 6.55 g of powdery solid. It was recrystallized from acetone to give methyl (2-exo-3-endo)-2-phenyl-8-cyclopropylmethyl-8-azabicyclo[3.2.1]octane-3-carboxylate, hydrochloride salt, needles, m.p. 198°–199° C. (decompn.).

EXAMPLE 27

Methyl (exo,exo)-8-(2-propyl)-2-(2-thienyl)-8-azabicyclo[3.2.1]octane-3-carboxylate was prepared by stirring a mixture of 5.02 g (0.020 mol) of methyl (exo,exo)-2-(2-thienyl)-8-azabicyclo[3.2.1]octane-3-carboxylate (Example 20), 5.04 g (0.060) mol) of solid sodium bicarbonate, 6.80 g (0.040 mol) of 2-iodopropane and 35 ml of dry dimethylformamide at room temperature for 3 days. Silica TLC (3:97 i-PrNH$_2$-Et$_2$O) showed incomplete reaction. More isopropyl iodide (6.8 g) and sodium bicarbonate (5 g) were added and the mixture was heated at 60°-70° C. with stirring for 9 hrs. TLC showed complete reaction. The dimethylformamide was removed by warming in vacuo, water was added and the mixture was extracted twice with ether. Addition of ethereal hydrogen chloride precipitated a gum which crystallized upon trituration with ether. One recrystallization of the resulting 5.1 g of salt from acetone gave 3.55 g of the title compound as its hydrochloride salt, blades and plates, m.p. 230°-231° C.

EXAMPLE 28

Methyl (exo,exo)-8-(1-butyl)-2-(2-thienyl)-8-azabicyclo[3.2.1]octane-3-carboxylate was prepared from 1-iodobutane and the N-hydrogen compound of Example 20 by the method used in Example 27 except that the reaction was complete at room temperature in 21 hrs. without addition of further reagents. When the precipitated hydrochloride salt failed to crystallize, it was treated with concentrated ammonium hydroxide and the liberated base was extracted with ether and distilled to give the title compound as a light amber oil, b.p. 148°-149.5° C. (0.03 mm), n$_D^{25}$=1.5322.

EXAMPLE 29

Methyl (exo,exo)-8-(1-pentyl)-2-(2-thienyl)-8-azabicyclo[3.2.1]octane-3-carboxylate was prepared from 1-iodopentane and the N-hydrogen compound of Example 20 by the method used in Example 28. Following distillation of the product at 147°-149° C. (0.2 mm), n$_D^{25}$=1.5269, it was found possible to prepare a crystalline methanesulfonate salt, m.p. 112°-115° C., colorless powder from isopropyl acetate.

EXAMPLE 30

Methyl (exo,exo)-8-(1-heptyl)-2-(2-thienyl)-8-azabicyclo[3.2.1]octane-3-carboxylate was prepared from 1-iodoheptane and the N-hydrogen compound of Example 20 in the same way as in Example 28 except that the reaction was run at 60° C. in 3 hrs. The product was obtained in the free base form, b.p. 160°-161° C. (0.15 mm), n$_D^{25}$=1.5205.

EXAMPLE 31

Methyl (exo,exo)-8-[1-(2-ethylbutyl)]-2-(2-thienyl)-8-azabicyclo[3.2.1]octane-3-carboxylate was prepared by stirring a mixture of 4.0 g (0.016 mol) of the N-hydrogen compound of Example 20, 4.2 g (0.05 mol) of solid sodium bicarbonate, 5.28 g (0.032 mol) of 3-bromomethylpentane and 25 ml of dimethylformamide at room temperature for 65 hrs. TLC (silica gel; 3:97 i-PrNH$_2$-Et$_2$O) showed only about 30% reaction. It was then heated at 60° C. for 48 hrs. whereupon it showed greater than 90% reaction. The mixture was concentrated by warming in vacuo, ether was added and the mixture was filtered. The filtrate yielded 6.4 g of oil which was chromatographed on basic alumina to remove starting material. The resulting 4.13 g of oil was distilled to give 3.57 g of the title compound, b.p. 147°-149° C. (0.2 mm).

EXAMPLE 32

Methyl (exo,exo)-8-(2-phenylethyl)-2-(2-thienyl)-8-azabicyclo[3.2.1]octane-3-carboxylate was prepared from 2-phenylethyl bromide and the N-hydrogen compound of Example 20 by the method used in Example 28. When stirring at room temperature for 66 hrs. produced only about 80% reaction, the mixture was heated at 70° C. for 5 hrs. to complete it. The liberated base was recrystallized twice from methanol to give the title compound, blades, m.p. 85°-86° C.

EXAMPLE 33

Methyl (exo,exo)-8-(2-hydroxyethyl)-2-(2-thienyl)-8-azabicyclo[3.2.1]octane-3-carboxylate The N-hydrogen compound of Example 20 (4.0 g, 0.012 mol) was added to a solution of 10 g (0.23 mol) of ethylene oxide and 1.6 g (0.017 mol) of phenol in 75 ml of acetonitrile and the solution was heated in an autoclave for 6 hrs. at 125° C. The mixture was concentrated by warming in vacuo and the residue was extracted with ether. The basic product was extracted from the ether with 2 N hydrochloric acid and liberated with concentrated ammonium hydroxide. A solution of the basic product in ether was treated with gaseous hydrogen chloride and the gummy precipitate was triturated with acetone to give a crystalline salt. Two recrystallizations from acetonitrile furnished the title compound as its hydrochloride salt, blades, m.p. 178°-180° C.

EXAMPLE 34

Methyl (exo,exo)-8-(3-hydroxypropyl)-2-(2-thienyl)-8-azabicyclo[3.2.1]octane-3-carboxylate was prepared starting with 4.0 g (0.016 mol) of the N-hydrogen compound of Example 20, 4.2 g (0.05 mol) of solid sodium bicarbonate, 25 ml of dimethylformamide and 5.80 g (0.032 mol) of 3-bromopropyl acetate. The mixture was stirred for 22 hrs. at room temperature, filtered, and the residue from concentration of the filtrate was purified by chromatography on 20 silica preparative plates (3:97 i-PrNH$_2$-Et$_2$O).

The resulting 5.0 g of 8-(3-acetoxypropyl) intermediate was dissolved in 70 ml of 2 N hydrochloric acid and the solution was heated under reflux for 24 hrs. Concentration by warming in vacuo gave 4.6 g of (exo,exo)-8-(3-hydroxypropyl)-2-(2-thienyl)-8-azabicyclo[3.2.1]octane-3-carboxylic acid. A solution of the latter in 50 ml of MeOH was saturated with gaseous hydrogen chloride and refluxed gently for 4 hrs. with a slow stream of hydrogen chloride bubbling into it. Concentration of the mixture by warming in vacuo, treatment with concentrated ammonium hydroxide and ether extraction gave 2.55 g of basic oil which was about 80% pure by tlc. It was chromatographed as above on 10 plates to give 1.80 g of the title compound. The latter was converted to its p-toluenesulfonate salt, m.p. 175°-176° C., prisms from acetonitrile.

EXAMPLE 35

Methyl (exo,exo)-8-(2-ethoxyethyl)-2-(2-thienyl)-8-azabicyclo[3.2.1]octane-3-carboxylate was prepared from 4.9 g (0.032 mol) of 2-bromoethyl ethyl ether and 4.0 g (0.016 mol) of the N-hydrogen compound of Example 20 in the same way as in Example 28 except that the reaction mixture was heated at 60° C. for 7 hrs. It was diluted with ether, filtered and the filtrate was concentrated by heating in vacuo. The residue was dissolved in 50 ml of ether and the solution was filtered free of a brown gum (0.3 g) and concentrated to a 10 ml volume. Addition of 20 ml of pentane and chilling caused precipitation of 1.85 g of the title compound, prisms, m.p. 62°–65° C.

EXAMPLE 36

Methyl (exo,exo)-8-(2,2-diethoxyethyl)-2-(2-thienyl)-8-azabicyclo[3.2.1]octane-3-carboxylate was prepared from 4.0 g (0.016 mol) of the N-hydrogen compound of Example 20 and 6.31 g (0.032 mol) of α-bromoacetaldehyde diethylacetal in the same way as in Example 28 except that the mixture was heated at 90°–100° C. for 4 hrs. The product distilled at 170°–172° C. (0.35 mm) (3.52 g). The product was precipitated from ether with gaseous hydrogen chloride and the base recovered with 5 N ammonium hydroxide to remove most impurities but chromatography on basic alumina (1:9 EtOAc-Hexane) was used for final purification. Pumping the resulting oil at 80°–85° C. gave 2.15 g of pure title compound, yellow liquid, b.p. 170°–172° C. (0.35 mm).

EXAMPLE 37

Methyl (exo,exo)-8-tetrahydrofurfuryl-2-(2-thienyl)-8-azabicyclo[3.2.1]octane-3-carboxylate was prepared from 5.02 g (0.020 mol) of the N-hydrogen compound of Example 20 and 6.6 g (0.040 mol) of tetrahydrofurfuryl bromide by the method used in Example 27. Stirring for 65 hrs. at 25° C. produced negligible reaction. When heating at 80° C. for 24 hrs. produced only 50% reaction, an additional 6.6 g of bromide and 5 g more sodium bicarbonate were added and heating at 80° C. continued for 15 hrs. With apparent 95% reaction, the mixture was diluted with 10 ml of water and extracted twice with ether. The extracts were washed with brine and concentrated to give 6.34 g of oil which was treated with 10 ml of acetic anhydride for 15 min. This solution was concentrated, the residue was dissolved in ether and the basic component was precipitated with hydrogen chloride. Treatment of the gummy salt with concentrated ammonium hydroxide, separation of the base with ether and distillation of this product afforded 5.03 g of the title compound, b.p. 160°–167° C. (0.2 mm), most of which boiled at 165°–167° C.

EXAMPLE 38

Methyl (exo,exo)-8-(2-cyanoethyl)-2-(2-thienyl)-8-azabicyclo[3.2.1]octane-3-carboxylate was prepared by refluxing a solution of 4.0 g (0.016 mol) of the N-hydrogen compound of Example 20 in 15 ml of acrylonitrile for 72 hrs. The solution was concentrated to a residue which was chromatographed on silica preparative plates to give 3.5 g of pure title compound. It was converted in EtOAc to a p-toluenesulfonate salt, m.p. 209°–211° C., prisms from acetonitrile.

EXAMPLE 39

Methyl (exo,exo)-3-methoxycarbonyl-2-(2-thienyl)-8-azabicyclo[3.2.1]octane-8-acetate A mixture of 3.32 g (0.010 mol) of the hydrobromide salt of the N-hydrogen compound of Example 20, 4.0 g (0.048 mol) of solid sodium bicarbonate and 25 ml of dimethylformamide was heated to 100° C. with stirring, and a solution of 3.06 g (0.020 mol) of methyl bromoacetate in 10 ml of dimethylformamide was added in 1 ml portions over a period of 10 min. Gas was evolved. The mixture was stirred and heated thus for 1 hr. and then distilled in vacuo to remove volatile solvent. The residue was treated with 10 ml of 2 N sodium hydroxide and extracted twice with ether. Addition of hydrogen chloride to the extracts precipitated a salt which crystallized upon trituration with acetone in which the crystalline salt is only slightly soluble. The title compound as the hydrochloride salt (1.70 g) crystallized as a hemihydrate, plates, m.p. 155°–156.5° C.

EXAMPLE 40

(exo,exo)-3-Methoxycarbonyl-2-(2-thienyl)-8-azabicyclo[3.2.1]octane-8-acetamide was prepared from 4.8 g (0.019 mol) of the N-hydrogen compound of Example 20 and 7.05 g (0.038 mol) of iodoacetamide by the method used in Example 27 except that the reaction was complete at room temperature in 3 hrs. without addition of further reagents. Following removal of the dimethylformamide the residue was treated with 25 ml of water and 40 ml of chloroform. The chloroform layer was washed twice with 10 ml portions of water and once with brine, concentrated to a 20 ml volume and treated with excess 3.5 N ethereal hydrogen chloride. Trituration of the gum with a few ml of acetone and dilution with 200 ml of ether gave 6.1 g of crystalline product. Recrystallization from 250 ml of 4:1 $CH_3CN$-EtOH boiled down to a 150 ml volume gave 3.5 g of the title compound as the hydrochloride salt, m.p. 233° C.

EXAMPLE 41

Ethyl (exo,exo)-8-(1-pentyl)-2-(2-thienyl)-8-azabicyclo[3.2.1]octane-3-carboxylate was prepared by hydrolyzing 6.10 g (0.019 mol) of the compound of Example 29 with hydrochloric acid and reesterifying with ethanol as in Example 15. The free base was liberated with ammonium hydroxide and distilled to give 5.23 g of pure title compound, b.p. 149°–153° C. (0.2 mm).

EXAMPLE 42

Methyl (exo,exo)-8-cyclopropylmethyl-2-phenyl-8-azabicyclo[3.2.1]octane-3-carboxylate was prepared from its 3-endo epimer (Example 26) by treating 4.5 g (0.0134 mol) of the latter (as its hydrochloride salt) in 35 ml of methanol with 1.0 g of sodium methoxide and refluxing the mixture for 4.5 hrs. The methanol was removed in vacuo, water and ether were added and the ether layer was concentrated to give 3.8 g of oil which contained (by NMR) 15% of unchanged 3-endo epimer. Chromatography of the sample on 15 preparative silica plates using 5:10:85 HCOOH-MeOH-$CHCl_3$ gave 2.76 g of pure title compound which formed a crystalline p-toluenesulfonate salt in ethyl acetate, m.p. 173°–176° C. when recrystallized from acetone.

EXAMPLE 43

(exo,exo)-1-[8-Methyl-2-(2-thienyl)-8-azabicyclo[3.2.1]octan-3-yl]ethanone

A stirred solution of 12.0 g (0.045 mol) of the pure exo,exo isomer of Example 10 in 100 ml of ether at 5°–10° C. was treated in 45 min. with 21.5 ml (0.056 mol) of 2.6 M ethereal methylmagnesium bromide which had been diluted with 100 ml of ether. The mixture was stirred for 1.5 hrs. at 10°–20° C. and poured into 50 ml of 2 N hydrochloric acid and 50 g of ice. The layers were separated and the ether layer was washed with 25 ml of 2 N hydrochloric acid. Washing of the acid portions with ether followed by basification afforded 11.3 g of oil which, upon dilution with 15 ml of pentane, precipitated 8.3 g of prisms. Treatment of these prisms in 20 ml of methanol with 19 g of sodium metabisulfite in 100 ml of water and extraction of this mixture with seven 30 ml portions of methylene dichloride gave 7.1 g of extracted oil. Plate chromatography of this oil (1:10:89 i-PrNH$_2$-Et$_2$O-pentane) gave 3.28 g of recovered starting material and 3.4 g of the desired ketone. Recrystallization from the latter 3.5 ml of cyclohexane with filtration by centrifugation gave 2.50 g of the title compound, m.p. 110.5°–112° C.; hydrochloride salt, m.p. 246°–247° C. (decompn.), plates from acetonitrile.

EXAMPLE 44

(exo,exo)-1-(8-Methyl-2-phenyl-8-azabicyclo[3.2.1]octan-3-yl)ethanone was prepared in the same manner and on the same scale as Example 43 but using the 2-phenyl ester of Example 1. The precipitate formed here upon Grignard addition was much heavier than that produced in Example 43. The crude base crystallized and, upon recrystallization from hexane, gave 6.82 g of needles of the title compound, m.p. 95°–97° C. The hydrochloride salt of this base was recrystallized twice from acetonitrile to give 4.67 g, prisms, m.p. 215°–216° C. (decompn.).

We claim:

1. A compound of the formula:

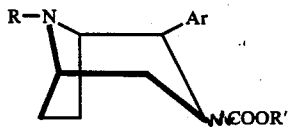

wherein:
R is selected from the group consisting of:
   hydrogen,
   alkyl of 1–8 carbon atoms optionally interrupted by an oxygen atom,
   phenylalkyl where alkyl has 1–3 carbon atoms,
   cyclopropylmethyl,
   hydroxyalkyl of 2–4 carbon atoms, and
   2,2-diethoxyethyl;
Ar is selected from the group consisting of:
   phenyl,
   benzyl,
   3-hydroxyphenyl,
   3-methoxyphenyl, and
   2-thienyl; and
R' is hydrogen or alkyl of 1 to 3 carbon atoms;
or a pharmaceutically acceptable acid-addition salt thereof.

2. A compound according to claim 1 wherein the COOR' group is in the exo configuration and Ar is phenyl.

3. A compound according to claim 1 wherein the COOR' group is in the exo configuration, R is methyl, R' is lower-alkyl of 1–3 carbon atoms and Ar is phenyl.

4. Methyl (exo,exo)-8-benzyl-2-phenyl-8-azabicyclo[3.2.1]octane-3-carboxylate, according to claim 2.

5. Methyl (exo,exo)-2-phenyl-8-azabicyclo[3.2.1]octane-3-carboxylate, according to claim 2.

6. Methyl (exo,exo)-8-cyclopropylmethyl-2-phenyl-8-azabicyclo[3.2.1]octane-3-carboxylate, according to claim 2.

7. Methyl (exo,exo)-8-methyl-2-(3-methoxyphenyl)-8-azabicyclo[3.2.1]octane-3-carboxylate, according to claim 1.

8. Methyl (exo,exo)-8-methyl-2-benzyl-8-azabicyclo[3.2.1]octane-3-carboxylate, according to claim 1.

9. (exo,exo)-8-Methyl-2-phenyl-8-azabicyclo[3.2.1]octane-3-carboxylic acid, according to claim 2.

10. A compound according to claim 1 wherein the COOR' group is in the exo configuration and Ar is 2-thienyl.

11. A compound according to claim 1 wherein the COOR' group is in the exo configuration, R is alkyl of 1–8 carbon atoms, R' is alkyl of 1–3 carbon atoms and Ar is 2-thienyl.

12. Methyl (exo,exo)-8-methyl-2-(2-thienyl)-8-azabicyclo[3.2.1]octane-3-carboxylate, according to claim 11.

13. Methyl (exo,exo)-8-(1-pentyl)-2-(2-thienyl)-8-azabicyclo[3.2.1]octane-3-carboxylate, according to claim 11.

14. Methyl (exo,exo)-8-(1-heptyl)-2-(2-thienyl)-8-azabicyclo[3.2.1]octane-3-carboxylate, according to claim 11.

15. Methyl (exo,exo)-8-[1-(2-ethylbutyl)]-2-(2-thienyl)-8-azabicyclo[3.2.1]octane-3-carboxylate, according to claim 11.

16. Ethyl (exo,exo)-8-(1-pentyl)-2-(2-thienyl)-8-azabicyclo[3.2.1]octane-3-carboxylate, according to claim 11.

17. Methyl (exo,exo)-8-(2-propyl)-2-(2-thienyl)-8-azabicyclo[3.2.1]octane-3-carboxylate, according to claim 11.

18. Methyl (exo,exo)-8-(1-butyl)-2-(2-thienyl)-8-azabicyclo[3.2.1]octane-3-carboxylate, according to claim 11.

19. A compound according to claim 1 wherein the COOR' group is in the exo configuration, R is hydrogen and Ar is 2-thienyl.

20. Methyl (exo,exo)-2-(2-thienyl)-8-azabicyclo[3.2.1]octane-3-carboxylate, according to claim 19.

21. (exo,exo)-2-(2-Thienyl)-8-azabicyclo[3.2.1]octane-3-carboxylic acid, according to claim 19.

22. Ethyl (exo,exo)-2-(2-thienyl)-8-azabicyclo[3.2.1]octane-3-carboxylate, according to claim 19.

23. Methyl (exo,exo)-8-(2-hydroxyethyl)-2-(2-thienyl)-8-azabicyclo[3.2.1]octane-3-carboxylate, according to claim 10.

24. Methyl (exo,exo)-8-(2-ethoxyethyl)-2-(2-thienyl)-8-azabicyclo[3.2.1]octane-3-carboxylate, according to claim 10.

25. Methyl (exo,exo)-8-(2-phenylethyl)-2-(2-thienyl)-8-azabicyclo[3.2.1]octane-3-carboxylate, according to claim 10.

26. Methyl (exo,exo)-8-(2,2-diethoxyethyl)-2-(2-thienyl)-8-azabicyclo[3.2.1]octane-3-carboxylate, according to claim 10.

27. Methyl (exo,exo)-8-(2-cyanoethyl)-2-(2-thienyl)-8-azabicyclo[3.2.1]octane-3-carboxylate.

28. Methyl (exo,exo)-3-methoxycarbonyl-2-(2-thienyl)-8-azabicyclo[3.2.1]octane-8-acetate.

29. Methyl (exo,exo)-8-tetrahydrofurfuryl-2-(2-thienyl)-8-azabicyclo[3.2.1]octane-3-carboxylate.

30. Methyl (exo,exo)-8-methyl-2-(1H-2-pyrrolyl)-8-azabicyclo[3.2.1]octane-3-carboxylate.

31. A compound according to claim 1 wherein the COOR' group is in the endo configuration and Ar is phenyl.

32. Methyl (2-exo-3-endo)-8-methyl-2-phenyl-8-azabicyclo[3.2.1]octane-3-carboxylate, according to claim 31.

33. Methyl (2-exo-3-endo)-2-phenyl-8-azabicyclo[3.2.1]octane-3-carboxylate, according to claim 31.

34. Methyl (2-exo-3-endo)-2-phenyl-8-cyclopropylmethyl-8-azabicyclo[3.2.1]octane-3-carboxylate, according to claim 31.

35. (2-exo-3-endo)-8-Methyl-2-phenyl-8-azabicyclo[3.2.1]octane-3-carboxylic acid, according to claim 31.

36. Methyl (2-exo-3-endo)-8-methyl-2-(3-methoxyphenyl)-8-azabicyclo[3.2.1]octane-3-carboxylate, according to claim 1.

37. Methyl (2-exo-3-endo)-8-methyl-2-benzyl-8-azabicyclo[3.2.1]octane-3-carboxylate, according to claim 1.

38. Methyl (2-exo-3-endo)-8-methyl-2-(3-hydroxyphenyl)-8-azabicyclo[3.2.1]octane-3-carboxylate, according to claim 1.

39. Methyl (2-exo-3-endo)-2-(3-hydroxyphenyl)-8-azabicyclo[3.2.1]octane-3-carboxylate, according to claim 1.

40. A process for preparing a compound according to claim 1 which comprises reacting a compound of the formula

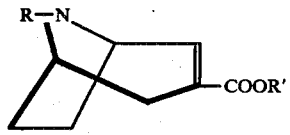

with ArMgX, where X is chlorine, bromine or iodine in an inert organic solvent under anhydrous conditions.

41. A process according to claim 40 wherein R is methyl or benzyl.

42. A process for preparing a compound according to claim 1 where R is other than hydrogen which comprises reacting a compound according to claim 1 where R is hydrogen with RX, where X is chlorine, bromine or iodine, in an inert organic solvent in the presence of a base.

* * * * *